(12) United States Patent
Pless et al.

(10) Patent No.: US 11,793,980 B2
(45) Date of Patent: Oct. 24, 2023

(54) INTESTINAL ATTACHMENT DEVICE

(71) Applicant: Celero Systems, Inc., Lincoln, MA (US)

(72) Inventors: Benjamin D. Pless, Lincoln, MA (US); Daniel Bacher, Walpole, MA (US)

(73) Assignee: CELERO SYSTEMS, INC., Lincoln, MA (US)

( * ) Notice: Subject to any disclaimer, the term of this patent is extended or adjusted under 35 U.S.C. 154(b) by 302 days.

(21) Appl. No.: 17/007,122

(22) Filed: Aug. 31, 2020

(65) Prior Publication Data
US 2021/0060318 A1 Mar. 4, 2021

Related U.S. Application Data

(60) Provisional application No. 62/894,725, filed on Aug. 31, 2019.

(51) Int. Cl.
*A61M 31/00* (2006.01)
*A61B 5/00* (2006.01)

(52) U.S. Cl.
CPC .............. *A61M 31/00* (2013.01); *A61B 5/42* (2013.01); *A61B 5/4839* (2013.01); *A61B 5/6861* (2013.01); *A61B 5/6873* (2013.01); *A61B 5/6882* (2013.01); *A61M 2205/18* (2013.01); *A61M 2205/32* (2013.01);
(Continued)

(58) Field of Classification Search
CPC ...... A61M 2205/32; A61M 2205/3306; A61M 2205/3584; A61M 2205/3303; A61M 31/00; A61M 31/002; A61M 2210/1042; A61B 5/42; A61B 5/4839; A61B 5/6861; A61B 5/6873; A61B 5/6882
See application file for complete search history.

(56) References Cited

U.S. PATENT DOCUMENTS 8,808,276 B2 8/2014 Boyden et al.
8,920,514 B2 12/2014 Gregory et al.
(Continued)

FOREIGN PATENT DOCUMENTS

EP 3756657 A1 * 12/2020 ............. A61B 5/065

OTHER PUBLICATIONS

Saxena, Payal et al. "Which clip? A prospective comparative study of retention rates of endoscopic clips on normal mucosa and ulcers in a porcine model." Saudi journal of gastroenterology : official journal of the Saudi Gastroenterology Association vol. 20,6 (2014): 360-5. doi:10.4103/1319-3767.145328.

*Primary Examiner* — Tasnim Mehjabin Ahmed
(74) *Attorney, Agent, or Firm* — TAROLLI, SUNDHEIM, COVELL & TUMMINO L.L.P.

(57) ABSTRACT

An intestinal attachment device is provided that includes an ingestible housing with a chamber having disposed therein a low-profile ribbon with a head that serves as a single attachment area for an anchor sized and configured to attach to the mucosal surface of an intestine. A disposable material is also disposed within the chamber and at least partially surrounds the ribbon. An anchor is disposed within the housing and is attached to the head of the low-profile ribbon. The anchor has a constrained and a non-constrained state and is sized and configured to attach to the mucosal surface of the intestine. The anchor is at least partially surrounded by a dissolvable material.

17 Claims, 5 Drawing Sheets

(52) U.S. Cl.
CPC ............... *A61M 2205/3306* (2013.01); *A61M 2205/3584* (2013.01); *A61M 2210/1042* (2013.01); *A61M 2230/04* (2013.01); *A61M 2230/42* (2013.01); *A61M 2230/50* (2013.01); *A61M 2230/63* (2013.01)

(56) References Cited

U.S. PATENT DOCUMENTS

| | | | |
|---|---|---|---|
| 9,320,721 B2 | 4/2016 | Vollmer | |
| 9,492,396 B2 | 11/2016 | Gross | |
| 2002/0165589 A1* | 11/2002 | Imran | A61N 1/0517 607/40 |
| 2002/0198470 A1* | 12/2002 | Imran | A61B 5/0084 600/587 |
| 2010/0286660 A1* | 11/2010 | Gross | A61B 5/4238 607/40 |
| 2015/0174076 A1 | 6/2015 | Harris et al. | |
| 2015/0335872 A1 | 11/2015 | Yang et al. | |
| 2016/0095821 A1 | 4/2016 | Finn et al. | |
| 2020/0323772 A1* | 10/2020 | Jones | A61K 9/0068 |

\* cited by examiner

INTESTINAL ATTACHMENT DEVICE

CROSS-REFERENCE TO RELATED APPLICATION

The present application claims priority to U.S. Provisional Application No. 62/894,725, filed on Aug. 31, 2019. The entirety of which is incorporated herein by reference.

TECHNICAL FIELD

The present disclosure relates to intestinal attachment devices that can be reside in the intestine for at least a temporary period of time.

BACKGROUND

There are many approaches for achieving adhesion with soft tissue such as the wall of the gastrointestinal tract. Chemical adhesives include cyanoacrylate, fibrin glues and biocompatible hydrogel adhesives. These approaches have been met with limited success due to the difficulties of using adhesives in the intestinal environment that includes the muscular action of peristalsis and the production of quantities of mucous. Mechanical fasteners include sutures, surgical staplers, and endoclips. Although such fasteners are effective, they can be difficult to apply to tissue. Sutures and staples are best suited for open, surgical procedures and are difficult to employ endoscopically. Endoclips are the only technology currently adapted for endoscopic use, but they leave behind a fairly large cylinder of metal and are not well suited for automatic deployment. As such, there exists a need for a gastrointestinal attachment device that is effective and convenient to deploy and that also provides a platform for other therapeutic applications such as drug delivery and sensors for physiological events.

SUMMARY

The present disclosure relates to an intestinal attachment device that can reside in the intestine of a patient for at least a day and up to several weeks. The device can be used as an anchoring device for a platform for delivering drugs into the intestine, sensing physiological parameters of the patient, releasing drugs in response to sensed physiological parameters, creating a physical barrier in the intestinal wall, and other applications.

In an aspect, an intestinal attachment device is provided that comprises an ingestible housing having an internal chamber. A low-profile ribbon can be disposed within the chamber and can have a head and a trailing portion extending from the head. The head can serve as a single attachment area for an anchor sized and configured to attach to the mucosal surface of an intestine. A dissolvable material can be disposed within the chamber and at least partially surrounding the ribbon. A fixation device can be disposed within the housing and can be sized and configured to attach to the mucosal surface of the intestine. An anchor can also be disposed within the housing and can be attached to the head of the low-profile ribbon. The anchor can have a constrained and a non-constrained state and can be sized and configured to attach to the mucosal surface of the intestine. A dissolvable material can at least partially surround the anchor.

In another aspect, an intestinal attachment device is provided that can comprise an ingestible housing defining a chamber and a port in fluid communication with the chamber. A propellent and a moveable anchor can be disposed within the chamber. The propellant can be in fluid communication with the moveable anchor such that when activated, the propellant advances the moveable anchor along a channel of the chamber towards the surface of an intestinal wall. A fixation device can be disposed within the housing and cam be sized and configured to attach to the mucosal surface of the intestinal wall. A biodegradable plug can be disposed within the port and is fabricated from a material that has a degradation time longer than the adherence time of the fixation device

DETAILED DESCRIPTION

As used herein with respect to a described element, the terms "a," "an," and "the" include at least one or more of the described elements including combinations thereof unless otherwise indicated. Further, the terms "or" and "and" refer to "and/or" and combinations thereof unless otherwise indicated. The terms "top" and "bottom" are with reference to components as illustrated in the figures. A "patient" as described herein includes a mammal, such as a human being. An "ingestible housing" as used herein is a housing that is not just capable of being ingested but rather is suitable for swallowing and entering into the gastrointestinal tract. In addition, when an element is referred to as being "attached to," "mounted on," "disposed on," "connected to," or in "communication with" another element, it can be directly attach to, mounted on, disposed on, connected to, or in communication with the other element or intervening elements may also be present unless otherwise indicated.

Figure 1:
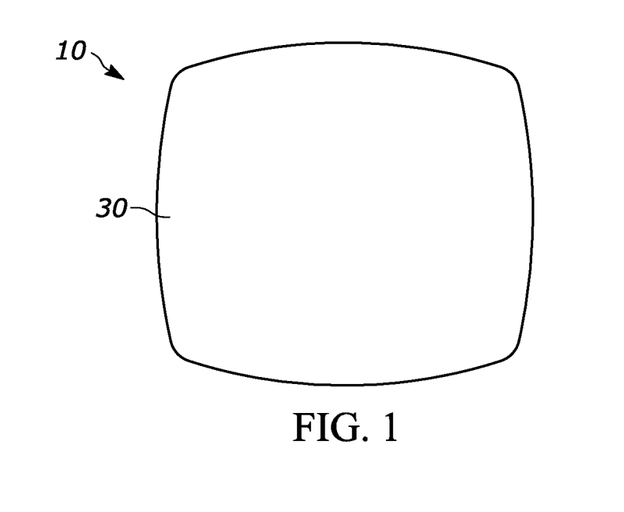
FIG. 1 is a top plan view of an intestinal attachment device according to an aspect of the present disclosure.
Figure 2:
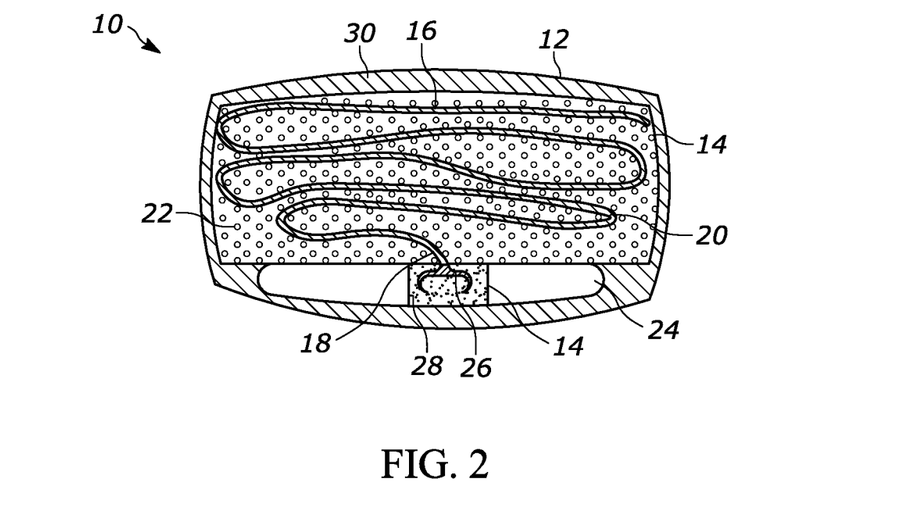
FIG. 2 is a cross-sectional view of an intestinal attachment device according to an aspect of the present disclosure.

Referring to FIGS. 1 and 2, an intestinal attachment device 10 is provided that comprises an ingestible housing 12 having an internal chamber 14. A low-profile ribbon 16 can be disposed within chamber 14 and can comprise a head 18 and a trailing portion 20 extending from the head. The head can serve as a single attachment area for an anchor sized and configured to attach to the mucosal surface of the patient's intestine. A dissolvable material 22 can be disposed within the chamber and can at least partially surround ribbon 16. A fixation device 24 can be disposed within housing 12. Fixation device 24 is illustrated as being located on the bottom of the housing but can be located on other surfaces so long as the fixation device can attach to the intestinal wall once reaching the intestine after ingestion. An anchor 26 can be disposed within housing 12 and can be attached to head 18 of ribbon 16. The anchor can be sized and configured to attach to the mucosal surface of the patient's intestine. Anchor 26 can have a constrained and a non-constrained state as described in more detail below. A dissolvable material 28 can at least partially surround anchor 26.

The ingestible housing can have various forms so long as the housing is suitable for ingestion. For example, the ingestible housing can be a gelatin capsule or can have another type of suitable enteric coating 30 that allows it to pass through the acidic environment of the stomach and then dissolve upon reaching the neutral pH environment of the intestine. Non-limiting examples of enteric coatings include cellulose acetate phthalate (CAP), poly(methacrylic acid-co-methyl methacrylate), cellulose acetate trimellitate (CAT), poly(vinyl acetate phthalate) (PVAP), or hydroxypropyl methylcellulose phthalate. The capsule can have any suitable size for swallowing such as between size 000 to size 4. The housing can also be a tablet as illustrated in FIG. 1 similar in configuration to tablets taken orally for ingestion of a drug. For example, the tablet can be approximately 10 mm long and approximately 7 mm thick.

Figure 3:
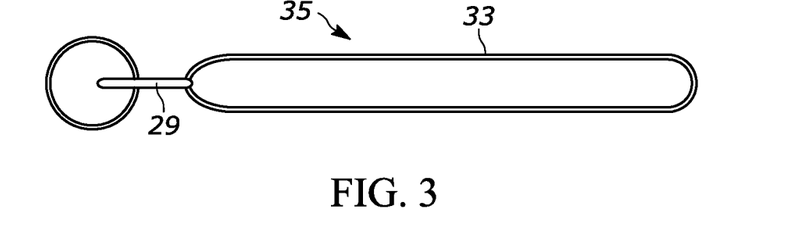
FIG. 3 is a side view of a fixation device, tether and a ribbon of an intestinal attachment device according to an aspect of the present disclosure.

The low-profile ribbon can be folded, rolled or otherwise packed into the chamber. The ribbon can be fabricated from a flexible material such as silk, cellulose, or polyimide, for example. The material can be biodegradable or non-biodegradable. Although the ribbon itself is low profile in the sense that it is thin and flat, it can have rigid sections and flexible sections therebetween. Such rigid sections can facilitate mounting of circuits or sensors on the ribbon. The head of the ribbon can serve as a single attachment area to the anchor as described in more detail below. As illustrated in FIG. 3, a ribbon 35 can include a radio-opaque strip 33 to facilitate locating the intestinal attachment device when using x-ray or CT imaging.

The ribbon can serve as a platform or substrate for a number of different components. For example, the ribbon can be a drug delivery device in which case the ribbon, or more particularly the trailing portion of the ribbon, can be impregnated with one or more therapeutic agents. As such, the ribbon can serve as a platform that is stable in the intestine for delivery of therapeutic agents for an extended period of time, such as for a week. The therapeutic agent can be delivered continuously, at fixed intervals, or on command from an external device. The device can contain a controller comprising electronic circuits that actuate drug release on a fixed schedule or in response to detection of a physiological event as described below. The ribbon can release therapeutic agents over a long period of time (e.g. over a period of a week) by a variety of mechanisms including bioerodable agents, iontophoresis, compartments that are commanded to open, or other mechanisms.

The ribbon can also be a sensing device in which case one or more sensors can be mounted or otherwise disposed on the ribbon, or more particularly the trailing portion of the ribbon, and can sense physiological events. Such sensors can include temperature sensors, acoustic sensors (e.g. to monitor cardiac or pulmonary function), electrical sensors (e.g. ECG or EMG sensors), chemical sensors, accelerometers (e.g. to sense position or movement), or suitable combinations thereof.

Figure 4:
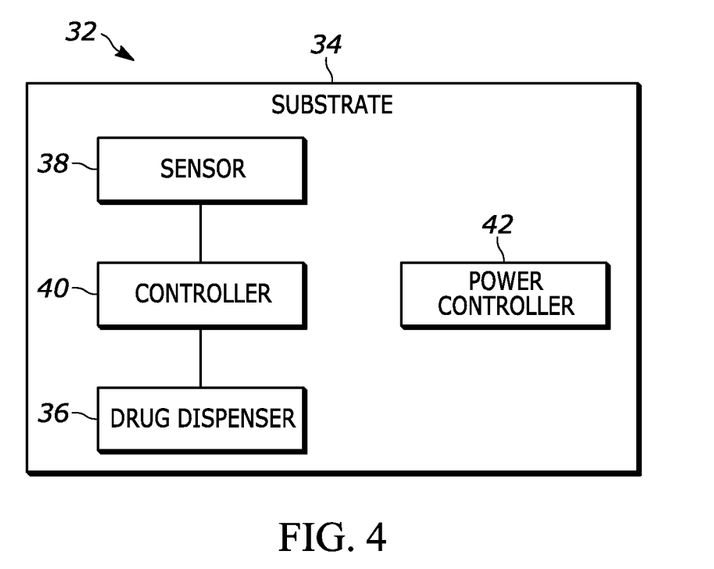
FIG. 4 is a block diagram of components of a ribbon of an intestinal attachment device according to an aspect of the present disclosure.

The ribbon can also include both sensors and therapeutic agents in which case the sensors can sense physiological parameters in the intestine and therapeutic agents can be released in the intestine in response to such sensed physiological parameters. For example, with reference to FIG. 4, a ribbon 32, and more particularly the trailing portion of the ribbon, can serve as a substrate 34 upon which a drug dispenser 36 and a sensor 38 are mounted. Sensor 38 can be configured to detect at least one physiological parameter indicative of a medical condition. A controller 40 can also be mounted on the ribbon that is operatively coupled to drug dispenser 36 and sensor 38. Controller 40 can be configured to receive a signal detected by sensor 38 of the physiological parameter to actuate release of the therapeutic agent from drug dispenser 36 into the patient's intestine upon a determination that the physiological parameter falls outside a threshold value or range. Ribbon 32 can also include a power controller 42 electrically connected to controller 40. Although FIG. 4 illustrates the drug dispenser as a separate component, such as a separate drug reservoir, the anchor can serve as the drug dispenser. For example, the anchor can be biodegradable and can be pre-loaded with a therapeutic agent that is released once the anchor biodegrades.

The ribbon can also include a wireless communication module to communicate with an external device to send out alerts to a caregiver or a patient as well as receive instructions from an external device. For example, the ribbon can include a Bluetooth radio that can communicate directly with a smart phone or other Bluetooth enabled device outside the patient's body. The Bluetooth radio can be a 2.4 GHz Bluetooth or a BLE (Bluetooth Low Energy) radio. The communication link can allow a physician to configure the intestinal attachment device to collect certain data and to retrieve the data after it has been collected. In an alternative configuration, wireless data telemetry can be achieved using a sub-GHz frequency radio (specifically 400-900 MHz, including 433 MHz radios) communicating to a small receiver, such as a key fob-sized receiver, that can be worn by the patient or otherwise placed on the patient's person that mediates data transfer between the intestinal attachment device and a smartphone via Bluetooth.

In certain aspects, the ribbon can be used to deliver an opioid antidote to mitigate the effects of an opioid overdose. In such instances, the ribbon can serve as a substrate upon which an electronic circuit is mounted. The ribbon can also include sensors that monitor one or more physiological parameters indicative of an opioid overdose such as electrical cardiac activity, heart rate, heart rate variability, respiratory monitoring (e.g. respiratory rate), saturated oxygen, intestinal tissue color, central temperature, bodily motions as detected from the intestine, or combinations thereof. Physiological parameters can be measured by an electrocardiogram (ECG) sensor, an accelerometer, a photoplethysmography (PPG) sensor, a temperature sensor, or combinations thereof. Upon detecting physiological indications of an opioid overdose, the ribbon can release a rescue medication via a drug dispenser disposed on the ribbon as well as send out alerts to the patient and/or a caregiver. Non limiting examples of suitable drug dispensers include MEMS drug delivery, valve systems, osmotic plug pistons, electrolytical pumps, or combinations thereof.

With respect to opioid overdose, the ribbon can include a non-refillable drug dispenser comprising an opioid antidote. An accelerometer and/or a PPG sensor can be disposed on the ribbon and can be configured to sense motion within the intestine and/or PPG data, respectively. A controller can be mounted on the ribbon and can be operatively coupled to the drug dispenser and the accelerometer and/or the PPG sensor. The controller can be configured to receive motion sensing data from the accelerometer and/or PPG data and estimate a respiratory rate of the patient based on the motion sensing data and/or the PPG data respectively and to actuate drug release of the opioid antidote from the drug dispenser into the intestine of the patient upon a determination that the respiratory rate falls outside a threshold value or range indicating that an opioid overdose has been detected. The device can also include a power controller electrically connected to the controller.

In the instance of drug delivery, the device may be passive in the sense that the device itself does not include an electrical power source or may incorporate a battery to provide power to electrical circuits disposed on the ribbon. The battery may be a conventional battery or an anode and cathode which, when exposed to the contents of the intestine, generate an electrical potential. For example, the anode may be magnesium, and the cathode may be copper chloride which results in a battery voltage of about 2.6 volt.

The ribbon can also serve as a temporary intestinal barrier that creates a physical barrier in the intestinal wall such that substances are not absorbed into the intestinal wall. For example, the ribbon can service as a physical barrier between receptors in the intestinal wall and food that directly affects key hormone levels. Such a physical barrier can be used for the treatment of diabetes, for example.

As stated above, the head of the ribbon can serve as a single attachment area for an anchor that is sized and configured to attach to the mucosal surface of the patient's intestine. Such a single attachment area has several advantages. The single attachment area can reduce the trauma and irritation on the intestine and also decrease the likelihood of the ribbon dislodging from the mucosal surface of the patient's intestine due to passing chyme or peristaltic movement. Regarding the latter, the intestine is muscular and moves vigorously and as such, if the anchor is attached at multiple points of a single head, this can place stress on the intestinal attachment device that can potentially tear out the anchor at the two or more attachment points. Such an occurrence can be avoided with a single attachment area even if there is significant intestinal movement. It should be noted that a head of the ribbon serves as a single attachment area but the ribbon can include a plurality of heads and the device can include a plurality of ribbons. By a head of a ribbon serving as a single attachment area means that for any given head of a ribbon, the anchor is not attached to such head at multiple points.

Regarding the fixation device that is disposed within the housing of the intestinal attachment device, the fixation device can be any suitable fixation device that is sized and configured to at least temporarily attach to the mucosal surface of the intestine. For example, the fixation device can be a mucoadhesive pad. FIG. 1 illustrates the fixation device as a mucoadhesive pad that defines a well 14. In this embodiment, anchor 26 is disposed in well 14 and dissolvable material 28 is also disposed in well 14 and at least partially surrounds anchor 26. The mucoadhesive pad can be fabricated from thiolated chitosan, or can include a hydrogel that contains or is largely formulated from a mucoadhesive such as poly(butadiene-maleic anhydride-co-L-DOPA) (PB-MAD) Carbopol or other suitable materials. The mucoadhesive pad can have a variety of shapes that allow the pad to adhere to the intestinal wall such as round, elongated, or digitated. The mucoadhesive pad or another type of fixation device can include therapeutic agents, such as anti-inflammatory agents or other medications, to minimize the impact on the intestinal wall.

Regarding the anchor that is also disposed in the housing, such an anchor can be any suitable anchor that can at least temporarily attach to the mucosal surface of the intestine. The anchor can transition from a constrained, mechanically stressed state to a non-constrained, mechanically relieved state. For example, the anchor can be "captured" in a dissolvable material that maintains the anchor in a constrained, mechanically stressed state. Once the material dissolves, such as by reacting with fluid in the intestine, the anchor can assume a non-constrained, mechanically relieved state such that the anchor can penetrate into the intestinal wall. The dissolvable material can be any suitable material such as mannitol or sodium polyacrylate, for example. Although the dissolvable material serves to maintain the anchor in a constrained state, it also keeps the sharp points of the anchor (in embodiments where the anchor has sharp ends) from scratching tissue prior to deployment. The anchor can be directly attached to the head of the ribbon or can be attached to a tether 29, which is attached to the head as illustrated in FIG. 3. FIG. 2 illustrates the anchor as a hook but the anchor can have other configurations, geometries, and mechanisms. For example, the anchor can be a barb, corkscrew, a suction device, or an adhesive. Although FIG. 2 illustrates the anchor as including two hooks, the anchor can include one or more anchoring members. Such anchoring members can extend circumferentially about the head of the ribbon, partially about the head of the ribbon or dispersed in the area of the head of the ribbon.

The anchor can be separate from any drug delivery system that is part of the intestinal attachment device or can be used as part of a drug delivery system. If used to deliver a therapeutic agent, the anchor can be fabricated from a material that takes longer than a week to erode in the body. The anchor can be fabricated from a material(s) such that it slowly erodes or erodes over a pre-determined period of time to allow for sustained release or prolonged of the therapeutic agent. Alternatively, the anchor can be fabricated from a material that allows for immediate release of the therapeutic agent. The device can include an anchor comprising multiple anchoring members with the same therapeutic agent, different concentration of the same therapeutic agent, different therapeutic agents, different concentrations of different therapeutic agents, etc. Non-limiting examples of fabrication materials for the anchor include magnesium, a magnesium alloy, or other non-toxic materials that are either inert or erode in the body. If the anchor is fabricated from pure magnesium, for example, it may be coated with a polymer to control the rate at which it erodes. The anchor can be a hollow needle defining a lumen having a distal end connected to a drug source such as a bladder or pump. Alternatively, the needle can be pre-loaded with a therapeutic agent such that once the needle erodes, the drug is released. The anchor can be deployed automatically once reaching the intestine or can be commanded to release to the intestine via a device external to the patient.

The intestinal attachment device can also include a sensor to confirm when the device has attached to the intestine and how secure the attachment is to intestine. For example, the device can include an impedance plethysmogram circuit to monitor the impedance across electrodes included in the device and automatically detect when the ribbon has been released from the housing. Furthermore, the signal from a photoplethysmography sensor can be monitored by the circuits for the presence of a physiological signal to confirm that the sensor is in contact with the wall of the intestine.

Figure 5:
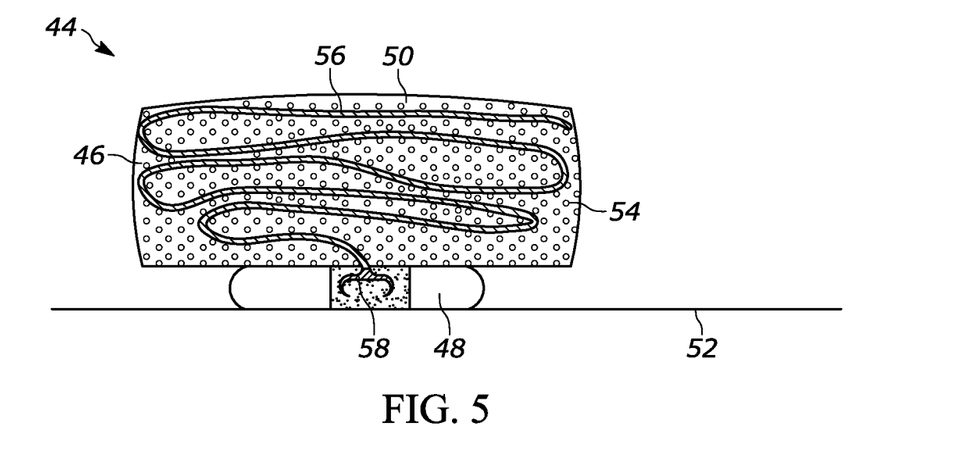
FIG. 5 is a cross-sectional view of an intestinal attachment device according to an aspect of the present disclosure illustrating one stage of deployment, namely after the intestinal attachment device has passed through the stomach. The enteric coating surrounding the chamber of the ingestible housing of the intestinal attachment device has dissolved and the mucoadhesive pad has attached the housing to the intestinal wall.
Figure 6:
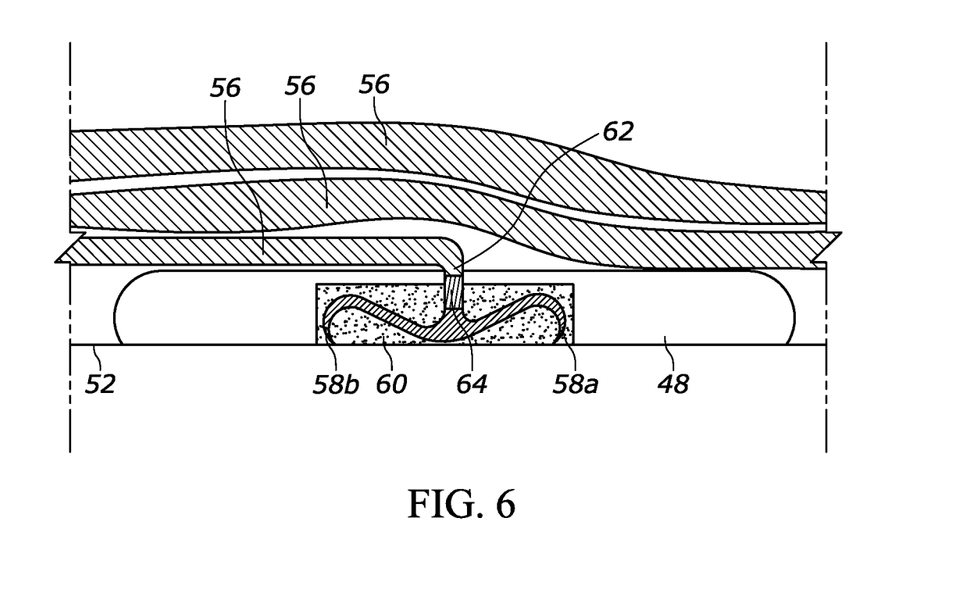
FIG. 6 is an enlarged view of components of an intestinal attachment device according to an aspect of the present disclosure with an anchor captured in a dissolvable material. The anchor is bent in a mechanically stressed and non-deployed position. In this aspect, the head of the ribbon is attached to the anchor via a tether.
Figure 7:
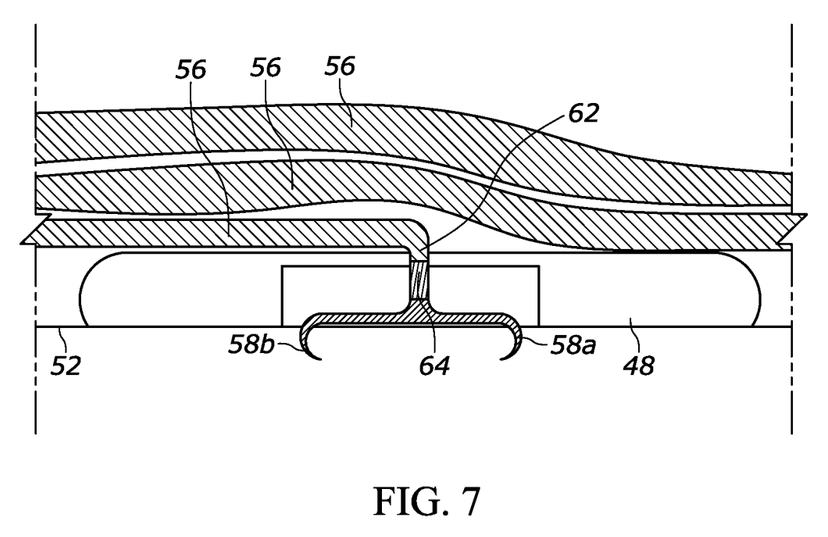
FIG. 7 is an enlarged view of the components of the intestinal attachment device of FIG. 6 with the anchor deployed into the intestinal wall. The anchor has transitioned to a mechanically relieved state.
Figure 8:
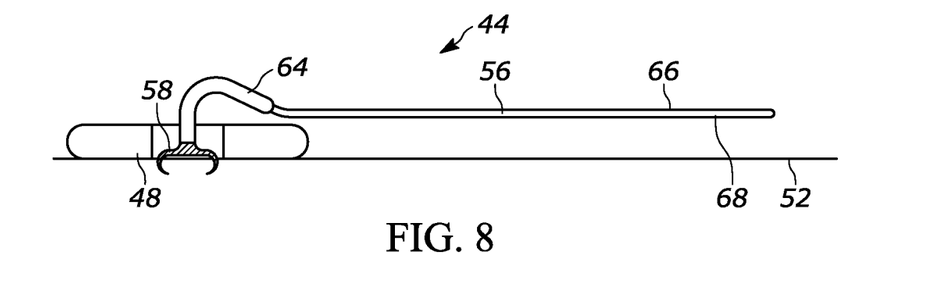
FIG. 8 is a side view of an intestinal attachment device according to an aspect of the present disclosure deployed in the intestine with the anchor attached to the intestinal wall.

FIGS. 5-8 illustrate an intestinal attachment device 44 during different stages of deployment. FIG. 5 illustrates the intestinal attachment device 44 after passage through the stomach. The enteric coating surrounding chamber 46 has dissolved and mucoadhesive pad 48 has attached the ingestible housing 50 to the intestinal wall 52. The material 54 surrounding ribbon 56 has not yet dissolved, but the time of such dissolution is not critical as anchor 58 has not yet been deployed. Mucoadhesive pad 48 adheres device 44 to intestinal wall 52 temporarily (e.g. for about an hour) until anchor 58 secures device 44 to intestinal wall 52 for a longer period of time. FIG. 6 is an expanded view of components of the intestinal attachment device including anchor 58, which in this case includes two opposing anchoring members 58a and 58b, captured in a dissolvable material 60. Anchoring members 58a and 58b are shown bent in a mechanically stressed and non-deployed position. When material 60 reacts with fluid in the intestine, anchoring members 58a and 58b will be effectively released and assume a mechanically relieved state and can penetrate into intestinal wall 52. In this embodiment, the head 62 of ribbon 56 is attached to anchoring members 58a and 58b via a tether 64. FIG. 7 illustrates anchoring members 58a and 58b deployed into intestinal wall 52. Material 60 has reacted with fluids in the intestine allowing the anchoring members 58a and 58b to assume a mechanically relieved state. In this example, the anchoring members penetrate about 0.3 mm into intestinal wall 52. FIG. 8 illustrates device 44 deployed in the intestine. Anchor 58 is attached to intestinal wall 52. Mucoadhesive pad 48 is still present but provides minimal attachment support to intestinal wall 52. Ribbon 56 has deployed (e.g. unfolded) and is connected to anchor 58 by tether 64. Ribbon 56 has one side 66 that is facing towards the lumen of the intestine and one side 68 that is facing towards intestinal wall 52. Each side may have different coatings with side 68 facing the intestinal wall 52 having, for example, a mucoadhesive coating, and side 66 facing towards the lumen of the intestine having, for example, a hydrophobic or an omniphobic coating. Drug delivery from ribbon 56 can be configured such that it is directed towards the lumen of the intestine or, alternatively, towards the wall of the intestine. For example, if the drug delivery is ionotophoretic, having the side containing the drug facing the intestinal wall will drive the drug into tissue. The anchoring members can be a vehicle for drug delivery and can bio-erode after approximately a week and the device can pass through the gastrointestinal tract of the patient.

The configuration and features of an intestinal attachment device provides several advantages. The ribbon is low profile such that the thickness of the ribbon is less than about a quarter of the diameter of intestinal lumen and thus is less susceptible to dislodgment from the intestinal wall. If instead of a ribbon, a bulky component extended into the lumen of the intestine, then passing chyme could push onto the bulky component and apply force to the anchor and potentially dislodge the anchor from the intestinal wall. Because of the low profile of the ribbon, it can resist the passing flow of chyme. In other words, the configuration of the ribbon provides low resistance to passing chyme reducing the stress on the anchor and lowering the likelihood of premature dislodgment of the anchor from the intestinal wall. Also, because of the single attachment area of the anchor to the ribbon and the intervening flexible tether, the ribbon extends down the lumen of the intestine once released from the chamber as illustrated in FIG. 8 and thus can easily move to provide the least resistance in response to peristaltic intestinal activity or other forces that deform the soft tissue of the intestine. Also, the flexible tether allows the ribbon to pivot at the attachment point providing geometric flexibility in attachment to the intestinal wall.

Figure 9:
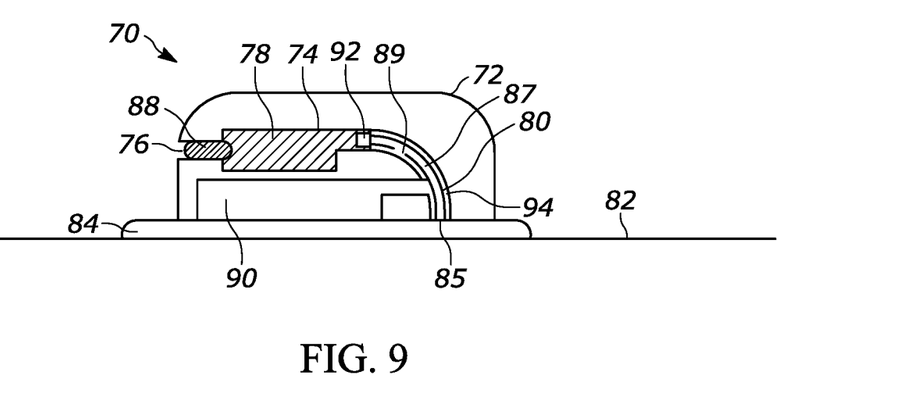
FIG. 9 is a cross-sectional view of an intestinal attachment device according to an aspect of the present disclosure in a non-deployed state.

Referring to FIG. 9, in another aspect, an intestinal attachment device 70 is provided that can include an ingestible housing 72 defining a chamber 74 and a port 76 in fluid communication with chamber 74. A propellant 78 and a moveable anchor 80 can be disposed in chamber 74. The propellant can comprise, for example, a super absorbent polymer, salt or other material that expands on contact with water or other fluid. Propellant 78 can be in fluid communication with moveable anchor 80. For example, moveable anchor 80 can be located in a region of the chamber, such as channel 79, distal to the region within which the propellant is disposed as illustrated in FIG. 9. The moveable anchor can be sized and configured to attach and/or penetrate the intestinal wall 82. A fixation device 84 can also be disposed within housing 72 and can be sized and configured to attach to intestinal wall 82. A biodegradable plug 88 can be disposed within port 76 and can be fabricated from a material that has a degradation time longer than the adherence time of fixation device 84. By this is meant that the plug takes longer to dissolve than it takes for the fixation device to adhere the ingestible housing to the intestinal wall to ensure that the ingestible housing is attached to the intestinal wall before the plug dissolves. The biodegradable plug can be fabricated from mannitol, for example.

As described in more detail below, the fixation device can be a mucoadhesive layer which causes the intestinal attachment device to adhere to the intestinal wall. The plug in the wall of the intestinal attachment device can dissolve upon exposure to intestinal fluid. As mentioned above, by design, the plug takes longer to dissolve than it takes for the intestinal attachment device to adhere to the intestinal wall to ensure that the intestinal attachment device adheres to the intestinal wall before the plug dissolves. When the plug dissolves and the port is exposed, intestinal fluid can access the propellant, which can be a super-absorbent material, causing the propellant to expand and thereby urge the anchor to penetrate into the intestinal wall thereby anchoring the intestinal attachment device to the intestine for a longer period of time than would be possible with just the mucoadhesive layer.

The ingestible housing can have various forms so long as the housing is suitable for ingestion as described above. For example, the ingestible housing can be a gelatin capsule or tablet or can have another type of suitable enteric coating that allows it to pass through the acidic environment of the stomach and then dissolve upon reaching the neutral pH environment of the intestine. Non-limiting examples of enteric coatings are provided above.

The intestinal attachment device can include various different components for different clinical applications. For example, the intestinal attachment device can be a drug delivery device and can provide an improved way to connect a drug delivery device to the wall of a bodily organ such as the wall of the intestine for example. In such an instance, the moveable anchor can be coated with a therapeutic agent. Alternatively, the moveable anchor can define an inner lumen 87 that is in fluid communication with a drug dispenser 90 as illustrated in FIG. 9 or the inner lumen can be pre-loaded with a therapeutic agent such that the anchor releases the therapeutic agent once the anchor biodegrades. With respect to the former, inner lumen 87 can have an inlet 89 at a proximal end thereof and an outlet 85 at a distal end thereof. As such, the anchor can be separate from any drug delivery system that is part of the intestinal attachment device or can be used as part of a drug delivery system. The therapeutic agent can be delivered continuously, at fixed intervals, or on command from an external device. For example, the intestinal attachment device can include a controller that contains electrical circuitry that is configured to actuate drug delivery continuously or at fixed intervals based on a drug delivery schedule. If used to deliver a therapeutic agent, the anchor can be fabricated from a material that takes longer than a week to erode in the body. The anchor can be fabricated from a material(s) such that it slowly erodes or erodes over a pre-determined period of time to allow for sustained release or prolonged of the therapeutic agent. Alternatively, the anchor can be fabricated from a material that allows for immediate release of the therapeutic agent. The device can include an anchor comprising multiple anchoring members with the same therapeutic agent, different concentration of the same therapeutic agent, different therapeutic agents, different concentrations of different therapeutic agents, etc. Non-limiting examples of fabrication materials for the anchor include magnesium, a magnesium alloy, or other non-toxic materials that are either inert or erode in the body. If the anchor is fabricated from pure magnesium, for example, it may be coated with a polymer to control the rate at which it erodes. The anchor can be a hollow needle defining a lumen having a distal end connected to a drug source such as a bladder or pump. Alternatively, as stated above, the needle can be pre-loaded with a therapeutic agent such that once the needle erodes, the drug is released. The anchor can be deployed automatically once reaching the intestine or can be commanded to release to the intestine via a device external to the patient. The device can contain electronic circuits that actuate drug release on a fixed schedule or in response to detection of a physiological event as described below.

The intestinal attachment device can also be a sensing device in which case one or more sensors can be mounted or otherwise disposed in the device and can sense physiological events. Such sensors can be contained within the ingestible housing or outside the ingestible housing but still within the intestinal attachment device. Such sensors can include temperature sensors, acoustic sensors (e.g. to monitor cardiac or pulmonary function), electrical sensors (e.g. ECG or EMG sensors), chemical sensors, accelerometers (e.g. to sense position or movement), or suitable combinations thereof.

The intestinal attachment device can also include both sensors and therapeutic agents in which case the sensors can sense physiological parameters in the intestine and therapeutic agents can be released in the intestine in response to such sensed physiological parameters. For example, the sensor can be configured to detect at least one physiological parameter indicative of a medical condition. The intestinal attachment device can also include a controller that is operatively coupled to the sensor and the moveable anchor or a drug dispenser in fluid communication with the moveable anchor. The controller can be configured to receive a signal detected by the sensor of the physiological parameter to actuate release of the therapeutic agent from the moveable anchor or the drug dispenser into the patient's intestine upon a determination that the physiological parameter falls outside a threshold value or range. The intestinal attachment device can also include a power controller electrically connected to the controller. The intestinal attachment device can also include a wireless communication module to communicate with an external device to send out alerts to a caregiver or a patient as well as receive instructions from an external device as described above.

In certain aspects, the intestinal attachment device can be used to deliver an opioid antidote to mitigate the effects of an opioid overdose. In such instance, the intestinal attachment device can include sensors that monitor one or more physiological parameters indicative of an opioid overdose such as electrical cardiac activity, heart rate, heart rate variability, respiratory monitoring (e.g. respiratory rate), saturated oxygen, intestinal tissue color, central temperature, bodily motions as detected from the intestine, or combinations thereof. Physiological parameters can be measured by an electrocardiogram (ECG) sensor, an accelerometer, a photoplethysograph (PPG) sensor, a temperature sensor, or combinations thereof. Upon detecting physiological indications of an opioid overdose, the intestinal attachment device can release a rescue medication via the moveable anchor as well as send out alerts to the patient and/or a caregiver. In certain instances, the sensor is an accelerometer and/or PPG sensor. A controller can be operatively coupled to the drug dispenser or the moveable anchor and the accelerometer and/or the PPG sensor. The controller can be configured to receive motion sensing data from the accelerometer and/or PPG data and estimate a respiratory rate of the patient based on the motion sensing data and/or the PPG data respectively and to actuate drug release of the opioid antidote from the moveable anchor into the intestine of the patient upon a determination that the respiratory rate falls outside a threshold value or range indicating that an opioid overdose has been detected. The device can also include a power controller electrically connected to the controller.

Regarding the fixation device that is disposed within the housing of the intestinal attachment device, the fixation device can be any suitable fixation device that is sized and configured to at least temporarily attach to the mucosal surface of the intestine. For example, the fixation device can be a mucoadhesive pad as described above.

Figure 10:
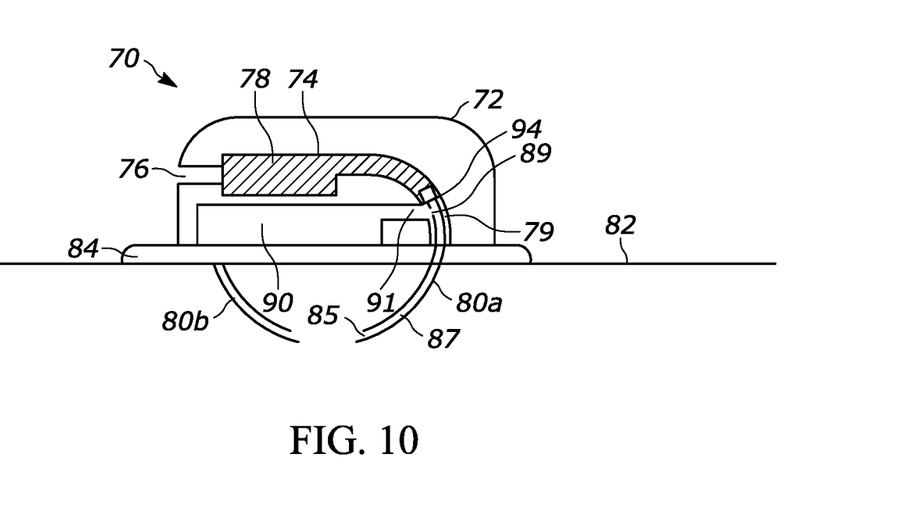
FIG. 10 is a cross-sectional view of an intestinal attachment device according to an aspect of the present disclosure in a deployed state.

Regarding the anchor that is also disposed in the housing, such an anchor can be any suitable anchor that can at least temporarily attach to the mucosal surface of the intestine. FIGS. 9 and 10 illustrate the anchor as a curved needle but the anchor can have other configurations and geometries suitable to engage the intestinal wall and provide sufficient anchoring to such wall. For example, the anchor can be a barb, hook, or corkscrew. The anchor can be substantially straight or curved. Although FIG. 10 illustrates the anchor as including two curved needles, the anchor can include one or more anchoring members. The anchor can be fabricated from a biodegradable material such as an iron or magnesium alloy.

The intestinal attachment device can also include a sensor to confirm when the device has attached to the intestine and how secure the attachment is to intestine. For example, the device can include a plethysmogram circuit to monitor the impedance across electrodes included in the device and automatically detect when the device has attached to the intestine as describe above.

FIG. 9 illustrates intestinal attachment device 70 after it was been swallowed by a patient and the enteric coating has dissolved in the upper intestine exposing fixation device 84, which in this embodiment is a mucoadhesive pad. Anchor 80 has not yet deployed and plug 88 is disposed in port 76. Anchor 80 is illustrated as having a needle-like quarter-circle configuration but could have other configurations so long as the anchor can provide sufficient anchoring to the intestinal wall. Anchor 80 has an inlet 89, an outlet 85 and a lumen 87 extending therebetween. Fixation device 84 adheres intestinal attachment device 70 securely in place while anchor 80 deploys into the intestinal wall. Once the anchor deploys, the fixation device is no longer needed and may dissolve or erode away while the intestinal attachment device still adheres to the intestinal tissue. This embodiment includes a drug dispenser 90 that is in fluid communication with inner lumen 87 of anchor 80, which acts like a needle to deliver drug directly into the intestine 82 of the patient. FIG. 10 illustrates intestinal attachment device 70 after anchor 80 has been deployed into the intestinal wall 82. Plug 88 has dissolved away thereby exposing port 76 through which intestinal fluid reaches propellant 78 in chamber 74. Propellant 78 has expanded to advance anchor 80 along channel 79 and has as largely filled channel 79. As anchor 80 is advanced along channel 79, inlet 89 is urged towards drug dispenser 90 until inlet 89 is in fluid communication with opening 91 of drug dispenser 90 such that the therapeutic agent contained within drug dispenser 91 enters into lumen 87 of anchor 80. The anchor can have an endcap 92 that engages a sleeve 94 of channel 79 to prevent anchor 80 from advancing past channel 79 and outside of intestinal attachment device 70. As shown, anchor 80 has advanced through the mucosal layer of intestinal wall 82 to engage the tissue in a hook-like fashion. FIG. 10 schematically depicts anchor 80 as including two anchoring members 80a and 80b for purposes of illustrating one embodiment of anchor 80. The therapeutic agent within lumen 87 of anchor 80 can flow through outlet 85 into the intestine.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Particularly, the aspects and features described with respect to FIGS. 1-8 can be included with aspects and features described with respect to FIGS. 9 and 10. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. An intestinal attachment device comprising:
    an ingestible housing having an internal chamber;
    a low-profile ribbon comprising a controller comprising an electrical circuit that is configured to actuate therapeutic agent release on a fixed schedule or in response to detection of a physiological event, the ribbon disposed within the chamber and having a head and a trailing portion extending from the head, the head serving as a single attachment area for an anchor sized and configured to attach to the mucosal surface of an intestine;
    a dissolvable material disposed within the chamber and at least partially surrounding the ribbon;
    a fixation device disposed within the housing;
    the anchor disposed within the housing and attached to the head of the low-profile ribbon, the anchor having a constrained state and a non-constrained state and sized and configured to attach to the mucosal surface of the intestine; and
    another dissolvable material at least partially surrounding the anchor.

2. The intestinal attachment device of claim 1, wherein the fixation device is a mucoadhesive pad defining a well and the anchor is disposed in the well.

3. The intestinal attachment device of claim 1, further comprising an enteric coating at least partially surrounding the chamber.

4. The intestinal attachment device of claim 1, further comprising a tether, the anchor attached to the head of the ribbon via the tether.

5. The intestinal attachment device of claim 1, wherein the ribbon comprises the therapeutic agent.

6. The intestinal attachment device of claim 1, wherein the ribbon comprises a sensor.

7. The intestinal attachment device of claim 1, wherein the ribbon comprises rigid sections and flexible sections, wherein the electrical circuit, a sensor, or combinations thereof are mounted on the rigid sections of the ribbon.

8. The intestinal attachment device of claim 1, wherein the ribbon comprises:
    a drug dispenser comprising the therapeutic agent;
    at least one sensor configured to detect at least one physiological parameter that has a threshold value or range indicative of a medical condition; and
    the controller being operatively coupled to the drug dispenser and the at least one sensor, the controller configured to receive a signal detected by the least one sensor of the at least one physiological parameter to actuate release of the therapeutic agent from the drug dispenser into the intestine of the patient upon a determination that the at least one physiological parameter falls outside the threshold value or range for the at least one physiological parameter.

9. The intestinal attachment device of claim 8, wherein the anchor serves as the drug dispenser.

10. The intestinal attachment device of claim 1, wherein the ribbon comprises:
    a drug dispenser comprising the therapeutic agent, the therapeutic agent comprising an opioid antidote;
    at least one sensor configured to detect at least one physiological parameter that has a threshold value or range indicative of an opioid overdose; and
    the controller being operatively coupled to the drug dispenser and the least one sensor, the controller configured to receive a signal detected by the least one sensor of the at least one physiological parameter to actuate release of the opioid antidote from the drug dispenser into the intestine of the patient upon a determination that the at least one physiological parameter falls outside the threshold value or range for the at least one physiological parameter indicating that an opioid overdose has been detected.

11. The intestinal attachment device of claim 1, wherein the ribbon comprises:
  a drug dispenser comprising the therapeutic agent, the therapeutic agent comprising an opioid antidote;
  an accelerometer configured to sense motion within the intestine; and
  the controller operatively being coupled to the drug dispenser and the accelerometer, the controller configured to receive motion sensing data from the accelerometer and estimate a respiratory rate of the patient based on the motion sensing data and to actuate release of the opioid antidote from the drug dispenser into the intestine of the patient upon a determination that the respiratory rate falls outside a threshold value or range indicating that an opioid overdose has been detected.

12. The intestinal attachment device of claim 1, wherein the ribbon comprises:
  a drug dispenser comprising the therapeutic agent, the therapeutic agent comprising an opioid antidote;
  a photoplethysmography (PPG) sensor configured to sense PPG data;
  the controller being operatively coupled to the drug dispenser and the PPG sensor, the controller configured to receive PPG sensing data from the PPG sensor and estimate a respiratory rate of the patient based on the PPG sensing data and to actuate release of the opioid antidote from the drug dispenser into the intestine of the patient upon a determination that the respiratory rate falls outside a threshold value or range indicating that an opioid overdose has been detected.

13. The intestinal attachment device of claim 1, wherein the ribbon comprises a radio-opaque strip.

14. The intestinal attachment device of claim 1, wherein the anchor is biodegradable.

15. The intestinal attachment device of claim 1, wherein the anchor is biodegradable and is pre-loaded with the therapeutic agent that is released once the anchor biodegrades.

16. The intestinal attachment device of claim 1, wherein the ribbon comprises a wireless communication module to communicate with an external device.

17. The intestinal attachment device of claim 1, wherein the therapeutic agent is disposed within the anchor.

* * * * *